(12) United States Patent
Noriega et al.

(10) Patent No.: US 7,381,198 B2
(45) Date of Patent: Jun. 3, 2008

(54) STEERABLE DISTAL SUPPORT SYSTEM

(75) Inventors: Gerardo Noriega, Mountain View, CA (US); Rudolfo Sudaria, Union City, CA (US)

(73) Assignee: Revascular Therapeutics, Inc., Sunnyvale, CA (US)

( * ) Notice: Subject to any disclaimer, the term of this patent is extended or adjusted under 35 U.S.C. 154(b) by 368 days.

(21) Appl. No.: 10/864,075

(22) Filed: Jun. 8, 2004

(65) Prior Publication Data
US 2005/0020974 A1    Jan. 27, 2005

Related U.S. Application Data

(63) Continuation-in-part of application No. 09/935,534, filed on Aug. 22, 2001, now Pat. No. 6,746,422.

(60) Provisional application No. 60/228,012, filed on Aug. 23, 2000.

(51) Int. Cl.
*A61M 31/00* (2006.01)
(52) U.S. Cl. ..................... 604/95.04; 606/194
(58) Field of Classification Search ............. 604/95.04, 604/104, 525, 526, 96.01, 95.01, 95.03, 523–528; 606/191, 192, 194
See application file for complete search history.

(56) References Cited

U.S. PATENT DOCUMENTS

| | | |
|---|---|---|
| 4,068,660 A | 1/1978 | Beck |
| 4,368,730 A | 1/1983 | Sharrock |
| 4,377,169 A | 3/1983 | Banks |
| 4,445,509 A | 5/1984 | Auth |
| 4,471,779 A | 9/1984 | Antoshkiw et al. |
| 4,490,421 A | 12/1984 | Levy |
| 4,516,972 A | 5/1985 | Samson |
| 4,534,363 A | 8/1985 | Gold |
| 4,538,622 A | 9/1985 | Samson et al. |
| 4,545,390 A | 10/1985 | Leary |
| 4,548,206 A | 10/1985 | Osborne |
| 4,554,929 A | 11/1985 | Samson et al. |
| 4,573,470 A | 3/1986 | Samson et al. |
| 4,586,923 A | 5/1986 | Gould et al. |
| 4,601,705 A | 7/1986 | McCoy |
| 4,613,385 A | 9/1986 | Thomas et al. |
| 4,616,653 A | 10/1986 | Samson et al. |
| 4,619,263 A | 10/1986 | Frisbie et al. |
| 4,641,654 A | 2/1987 | Samson et al. |
| 4,646,719 A | 3/1987 | Neuman et al. |
| 4,646,742 A | 3/1987 | Packard et al. |

(Continued)

OTHER PUBLICATIONS

U.S. Appl. No. 10/950,161, filed Sep. 24, 2004.

*Primary Examiner*—Nicholas D. Lucchesi
*Assistant Examiner*—Theodore J Stigell
(74) *Attorney, Agent, or Firm*—Townsend and Townsend and Crew LLP (57) ABSTRACT

A steerable distal support system for accessing stenosis, partial occlusions, or complete occlusions within a body lumen. The steerable distal support system generally includes an elongate member that comprises a proximal portion, a more flexible intermediate portion and a deflectable distal tip. The deflectable distal tip is at a distal end of the elongate body to facilitate directionality and positioning of the steerable distal support system to the target site. Optionally, an expandable centering assembly may be disposed on the steerable support assembly to center and anchor the steerable support assembly within the body lumen.

12 Claims, 12 Drawing Sheets

U.S. PATENT DOCUMENTS

| | | | |
|---|---|---|---|
| 4,676,249 A | 6/1987 | Arenas et al. |
| 4,708,717 A | 11/1987 | Deane et al. |
| 4,708,718 A | 11/1987 | Daniels |
| 4,715,378 A | 12/1987 | Pope, Jr. et al. |
| 4,717,387 A | 1/1988 | Inoue et al. |
| 4,719,924 A | 1/1988 | Crittenden et al. |
| 4,721,117 A | 1/1988 | Mar et al. |
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,798,598 A | 1/1989 | Bonello et al. |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,923,462 A | 5/1990 | Stevens |
| 4,925,445 A | 5/1990 | Sakamoto et al. |
| 4,926,858 A | 5/1990 | Gifford, III et al. |
| 4,940,062 A | 7/1990 | Hampton et al. |
| 4,946,466 A | 8/1990 | Pinchuk et al. |
| 4,953,553 A | 9/1990 | Tremulis |
| 4,990,134 A | 2/1991 | Auth |
| 5,021,044 A | 6/1991 | Sharkawy |
| 5,030,204 A | 7/1991 | Badger et al. |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |
| 5,107,852 A | 4/1992 | Davidson et al. |
| 5,115,814 A | 5/1992 | Griffith et al. |
| 5,116,350 A | 5/1992 | Stevens |
| 5,144,959 A | 9/1992 | Gamble et al. |
| 5,165,421 A | 11/1992 | Fleischhacker et al. |
| 5,174,276 A | 12/1992 | Crockard |
| 5,176,661 A | 1/1993 | Evard et al. |
| 5,178,158 A | 1/1993 | de Toledo |
| 5,184,627 A | 2/1993 | de Toledo |
| 5,195,971 A | 3/1993 | Sirhan |
| 5,209,727 A | 5/1993 | Radisch, Jr. et al. |
| 5,211,636 A | 5/1993 | Mische |
| 5,217,482 A | 6/1993 | Keith |
| 5,250,034 A | 10/1993 | Appling et al. |
| 5,267,979 A | 12/1993 | Appling et al. |
| 5,304,131 A * | 4/1994 | Paskar ................ 604/95.04 |
| 5,306,252 A | 4/1994 | Yutori et al. |
| 5,314,438 A | 5/1994 | Shturman |
| RE34,695 E | 8/1994 | Mar et al. |
| 5,345,945 A | 9/1994 | Hodgson et al. |
| 5,346,473 A | 9/1994 | Bowman |
| 5,368,035 A | 11/1994 | Hamm et al. |
| 5,377,690 A | 1/1995 | Berthiaume |
| 5,381,782 A | 1/1995 | DeLaRama et al. |
| 5,456,667 A * | 10/1995 | Ham et al. ................ 604/107 |
| 5,462,523 A | 10/1995 | Samson et al. |
| 5,484,407 A | 1/1996 | Osypka |
| 5,527,298 A | 6/1996 | Vance et al. |
| 5,527,326 A | 6/1996 | Hermann et al. |
| 5,569,197 A | 10/1996 | Helmus et al. |
| 5,571,085 A | 11/1996 | Accisano, III |
| 5,591,142 A | 1/1997 | Van Erp |
| 5,606,981 A | 3/1997 | Tartacower et al. |
| 5,611,777 A | 3/1997 | Bowden et al. |
| 5,662,671 A | 9/1997 | Barbut et al. |
| 5,772,609 A | 6/1998 | Nguyen et al. |
| 5,776,114 A | 7/1998 | Frantzer |
| 5,820,591 A | 10/1998 | Thompson et al. |
| 5,843,103 A | 12/1998 | Wulfman |
| 5,848,986 A | 12/1998 | Lundquist et al. |
| 5,860,938 A | 1/1999 | LaFontaine et al. |
| 5,865,800 A | 2/1999 | Mirarchi et al. |
| 5,868,685 A | 2/1999 | Powell et al. |
| 5,897,567 A | 4/1999 | Ressemann et al. |
| 5,908,395 A | 6/1999 | Stalker et al. |
| 6,001,112 A | 12/1999 | Taylor |
| 6,022,336 A | 2/2000 | Zadno-Azizi et al. |
| 6,050,972 A | 4/2000 | Zadno-Azizi et al. |
| 6,059,767 A | 5/2000 | Noriega |
| 6,066,149 A | 5/2000 | Samson et al. |
| 6,068,623 A | 5/2000 | Zadno-Azizi et al. |
| 6,093,157 A | 7/2000 | Chandrasekaran |
| 6,152,909 A | 11/2000 | Bagaoisan et al. |
| 6,156,046 A | 12/2000 | Passafaro |
| 6,179,851 B1 | 1/2001 | Barbut et al. |
| 6,183,432 B1 | 2/2001 | Milo |
| 6,217,567 B1 | 4/2001 | Zadno-Azizi et al. |
| 6,258,052 B1 | 7/2001 | Milo |
| 6,299,622 B1 | 10/2001 | Snow |
| 6,312,438 B1 | 11/2001 | Adams |
| 6,355,014 B1 | 3/2002 | Zadno-Azizi et al. |
| 6,375,628 B1 | 4/2002 | Zadno-Azizi et al. |
| 6,482,221 B1 | 11/2002 | Hebert et al. |
| 6,500,130 B2 | 12/2002 | Kinsella et al. |
| 6,585,717 B1 | 7/2003 | Wittenberger et al. |
| 6,602,264 B1 | 8/2003 | McGurckin |
| 6,743,208 B1 | 6/2004 | Coyle |
| 6,746,422 B1 | 6/2004 | Noriega et al. |
| 6,824,550 B1 | 11/2004 | Noriega et al. |
| 2004/0102719 A1 | 5/2004 | Keith et al. |

\* cited by examiner

STEERABLE DISTAL SUPPORT SYSTEM

CROSS-REFERENCES TO RELATED APPLICATIONS

The present invention is a continuation-in-part application of U.S. patent application Ser. No. 09/935,534, now U.S. Patent No. U.S. Pat. No. 6,746,422, which claims the benefit of U.S. Provisional Application No. 60/228,012, filed Aug. 23, 2000, the complete disclosures of which are incorporated herein by reference.

The present application is also related to U.S. patent application Ser. No. 09/030,657, filed Feb. 25, 1998, now U.S. Pat. No. 6,059,767, U.S. Provisional Patent Application No. 60/195,154, filed Apr. 6, 2000, and U.S. patent application Ser. No. 09/644,201, filed Aug. 22, 2000, the complete disclosures of which are incorporated herein by reference.

BACKGROUND OF THE INVENTION

The present invention is generally related to medical devices and methods. More specifically, the present invention provides a steerable distal support system for accessing stenosis, partial occlusions, or total occlusions in a patient's body lumen.

Cardiovascular disease frequently arises from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging, but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, the catheters used for these interventions must be introduced over a guidewire, and the guidewire must be placed across the lesion prior to catheter placement. Initial guidewire placement, however, can be difficult or impossible in tortuous regions of the vasculature. Moreover, it can be equally difficult if the lesion is total or near total, i.e. the lesion occludes the blood vessel lumen to such an extent that the guidewire cannot be advanced across.

For these reasons, it is desired to provide devices and methods which can access small, tortuous regions of the vasculature. In particular, it is desired to provide systems which can access partial occlusions, total occlusions, stenosis, blood clots, or thrombotic material.

SUMMARY OF THE INVENTION

The present invention provides a steerable distal support system that may be used as a working channel for a variety of different interventional devices. The steerable distal support systems of the present invention includes an elongate body comprising deflectable distal tip that can allow the working channel to be steered through the body lumen.

The steerable distal support system of the present invention may be used as a support or access system and can be navigated to and positioned at the target site, with or without the use of a separate guidewire. The steerable distal support system of the present invention provides the flexibility, maneuverability, torqueability (usually 1:1), and columnar strength necessary for accurately advancing through the tortuous vasculature either over a standard guidewire or on its own. In embodiments, in which the proximal port assembly is removable, the steerable distal support system itself may be considered to be a hollow guidewire.

Many thin walled polymeric based catheters do not have sufficient maneuverability or torqueability to be advanced through tortuous body lumens on their own and must be navigated to an occlusion over a standard guidewire. In order for these polymeric catheters to be used as working channels, to physically support devices inserted within the catheter lumen intended to penetrate or otherwise treat such lesions, the wall thickness must be increased, which results in a reduction of the size of the inner axial lumen. In contrast, the steerable distal support systems of the present invention typically has a thin wall construction while still providing sufficient torqueability and maneuverability to be advanced through the body lumen, either over a standard guidewire or on its own. Consequently, the thin coil walls allows the axial lumen of the working channel to be maximized. This allows larger diameter devices to be inserted into the axial lumen than can be inserted into conventional polymeric based catheters. The larger lumen of the steerable distal support system of the present invention allows devices such as rotating guidewire or drive shafts, infusion guidewire, clot maceration guidewires, normal guidewires of varying stiffness clot macerators and other larger devices to be delivered to the target occlusion. Additionally, the larger diameter lumen of the steerable distal support system allows for infusion of clot dissolving or other fluids, and for aspiration of debris stirred up in the clot maceration process.

Unlike conventional infusion and catheter devices, the steerable distal support system encompassed by the present invention may have a steerable distal tip which has the same diameter as the rest of the elongate body. Additionally, a radio-opaque marker can be positioned on the extreme distal tip of the catheter. This allows the user to precisely identify the position of the distal tip of the device. Identification of the precise location of the extreme distal tip is advantageous as it allows devices inserted into the working channel to be positioned precisely at the front surface of the occlusion or stenosis.

The steerable distal support systems of the present invention typically includes an elongate body comprising a proximal portion, a distal portion, and a steerable or deflectable distal tip. The deflectable distal tip can be coupled or integrally formed with rest of the elongate body. In some embodiments, the distal tip will optionally have ribs or slots to facilitate deflection in the desired direction. The ribs can be even or tapered.

The steerable distal support system includes at least one pull wire that can extend through the elongate body to couple to the one or more portions of the distal tip. The pull wire is offset from a longitudinal axis of the distal tip and elongate body, such that axial manipulation of the pull wire deflects the distal tip in a desired direction. By torquing or twisting a proximal end of the steerable distal support system the deflected tip can be steered and advanced through the tortuous regions of the vasculature.

In use, the steerable distal support system may be advanced through the body lumen to the occlusion. Steering or deflection of the distal tip controls the position and orientation of the distal tip disposed within the body lumen and can avoid perforating the body lumen wall. For example, if the steerable distal support system is navigated to the occlusion and the distal tip of the steerable distal support system is pointed in a direction toward the vessel wall, the direction of the distal tip can be changed by deflecting the distal tip and torquing and twisting the proximal end of the steerable distal support system.

In one embodiment, the present invention provides a steerable distal support system. The system comprises a hollow unibody elongate body comprising an integral proximal portion, intermediate portion, and a deflectable distal tip. The proximal portion is stiffer than the intermediate portion. A proximal housing is coupled to the proximal portion of the elongate body. A pull wire extends through an axial lumen of the elongate body from the proximal housing to the deflectable distal tip. Proximal actuation of the pull wire deflects the deflectable distal tip.

At least a portion of the intermediate portion may comprise spiral etchings (formed with a laser or wire electronic discharge machine (EDM)) so that at least a portion of the intermediate portion comprise a spiral coil. The spiral coil in the intermediate portion typically comprises a decreasing pitch distally along the intermediate portion so as to create an increased flexibility in the intermediate portion of the elongate body.

Because the intermediate portion has laser etched spiral openings, the steerable distal support system typically comprises at least one of an inner liner and an outer liner coupled to at least a portion of at least one of an inner surface and outer surface of the intermediate portion and the deflectable distal tip. The liner is typically in the form of a tubing, which are positioned to maintain a substantially fluid tight axial lumen from the proximal portion to the distal tip.

In a specific configuration, the elongate body (e.g., proximal portion, intermediate portion, and distal tip) is comprised of a single laser etched hypotube.

To improve the tracking of the steerable distal support system, the steerable distal tip may comprise a radiopaque marker disposed on a distal end. To improve deflection, the deflectable distal tip may comprise ribs to facilitate deflection of the deflectable distal tip. In some configurations, the ribs are tapered toward a distal end of the deflectable distal tip.

Optionally, the steerable distal support system may further comprise an expandable centering assembly, such as an expandable basket, that is positioned between the intermediate portion and the steerable distal tip. In preferred configurations, the proximal portion, intermediate portion, expandable centering assembly, and steerable distal tip are comprised of a single hypotube. The expandable centering assembly typically comprises a plurality of even spaced struts that are separated by slots. The expandable centering assembly in an expanded configuration is configured to engage an inner surface of a body lumen wall, wherein in the expanded configuration the struts are separated by the slots so as to allow fluids to flow around the struts and through the slots.

These and other aspects of the invention will be further evident from the attached drawings and description of the embodiments of the invention.

DESCRIPTION OF THE SPECIFIC EMBODIMENTS

Figure 11:
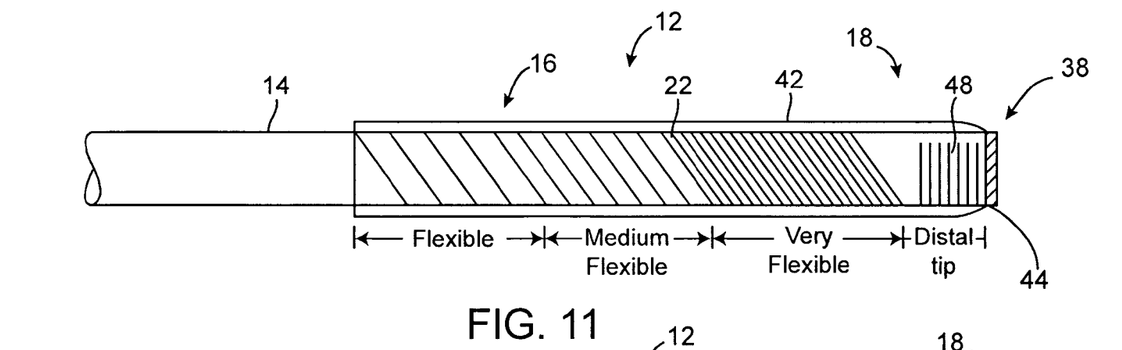
FIG. 11 illustrates a unibody embodiment of the steerable distal support system encompassed by the present invention.
Figure 13:
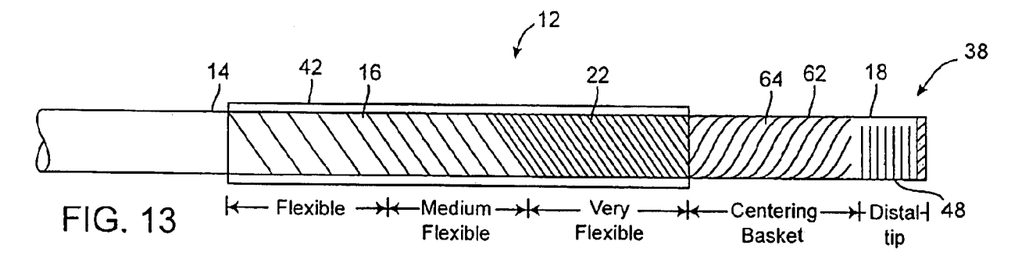
FIG. 13 illustrates yet another embodiment of a steerable distal support system that includes an expandable basket positioned on the distal end of the catheter.

The present invention provides a steerable distal support system that is in the form of catheter or hollow guidewire so as to define a working channel for an interventional device. The steerable distal support system of the present invention is typically comprised of one or more tubular bodies such as hypotubes. At least some of the hypotubes may be selectively etched to create spiral etchings that have a varying pitch along the length of the steerable distal support system so as to create one or more flexible, soft atraumatic coils. By varying the pitch of the spiral coils, a user may selectively create stiff and flexible portions along the length of the steerable distal support system. As will be described in greater detail below, the steerable distal support system in FIG. 1 comprises three separate coils coupled to each other to form the elongate body of the steerable distal support system. In contrast, the embodiments of FIGS. 11 and 13 are comprised of a single laser etched hypotube.

As can be appreciated, the present invention is not limited to the use of a hypotube to form the elongate body of the present invention. As can be appreciated, other material may be used to form the elongate body. For example, the elongate body may be comprised of one or more tubes of cobalt-chromium or nitinol. Moreover, if desired the proximal portion, intermediate portion, and distal flexible tip may be composed of different tubes that have different properties (e.g., different wall thicknesses, diameters, etc.).

Steerable distal support system is typically sized to be inserted through coronary, neuro, or peripheral arteries and may have a variety of wall thicknesses, diameters, and lengths. However, in preferred embodiments, the steerable distal support system typically has a wall thickness between about 0.002 inches and about 0.006 inches, but may incorporate any thickness that is practical. The outer diameter of the steerable distal support system may be constant along the length of the elongate body or it may taper distally. In either embodiment, the outer diameter of the elongate body is typically between approximately 0.014 inches and approximately 0.039 inches and preferably between approximately 0.021 inches and approximately 0.039 inches. The length of the steerable distal support system may be varied to correspond to the distance between the percutaneous access site and the target site. For example, for a target site within the heart that is being accessed through the femoral artery, the steerable distal support system will typically have a length of approximately 190 cm. It should be noted however, that other embodiments of the steerable distal support system may have dimensions that are larger or smaller than the above described embodiments and the present invention is not limited to the above recited dimensions.

The elongate body of the steerable distal support system preferably has a flexibility, pushability, and torqueability (typically 1:1) to allow a user to advance the steerable distal support system directly through a tortuous blood vessel to a target site. Because of the high columnar strength of the elongate body there is typically no need for a separate guidewire to advance the steerable distal support system through the body lumen to the occlusion. However, as can be appreciated, to ease delivery of the steerable distal support system to the target site, a separate guidewire may be used, if desired. Most embodiments of the steerable system includes a deflectable tip which provides improved directional control of the steerable distal support system and any device disposed within the lumen of the steerable distal support system.

Figure 1:
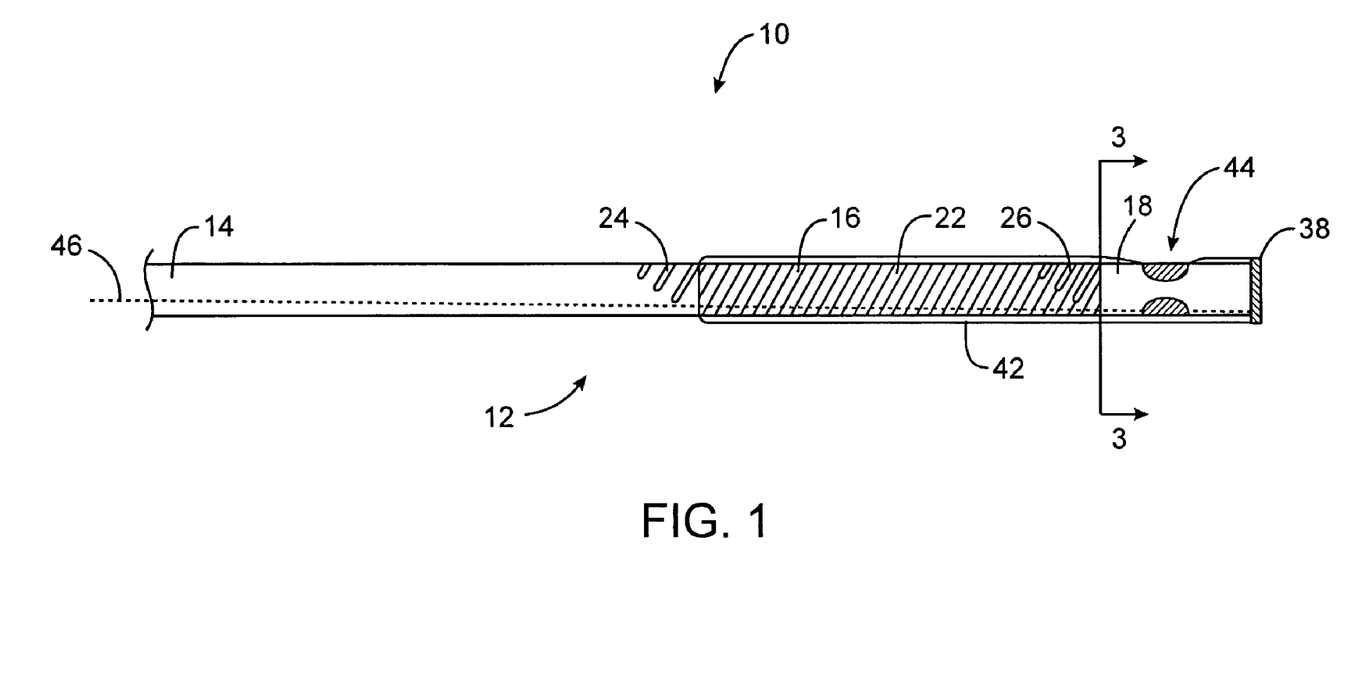
FIG. 1 shows a steerable distal support system encompassed by the present invention.
Figure 2:
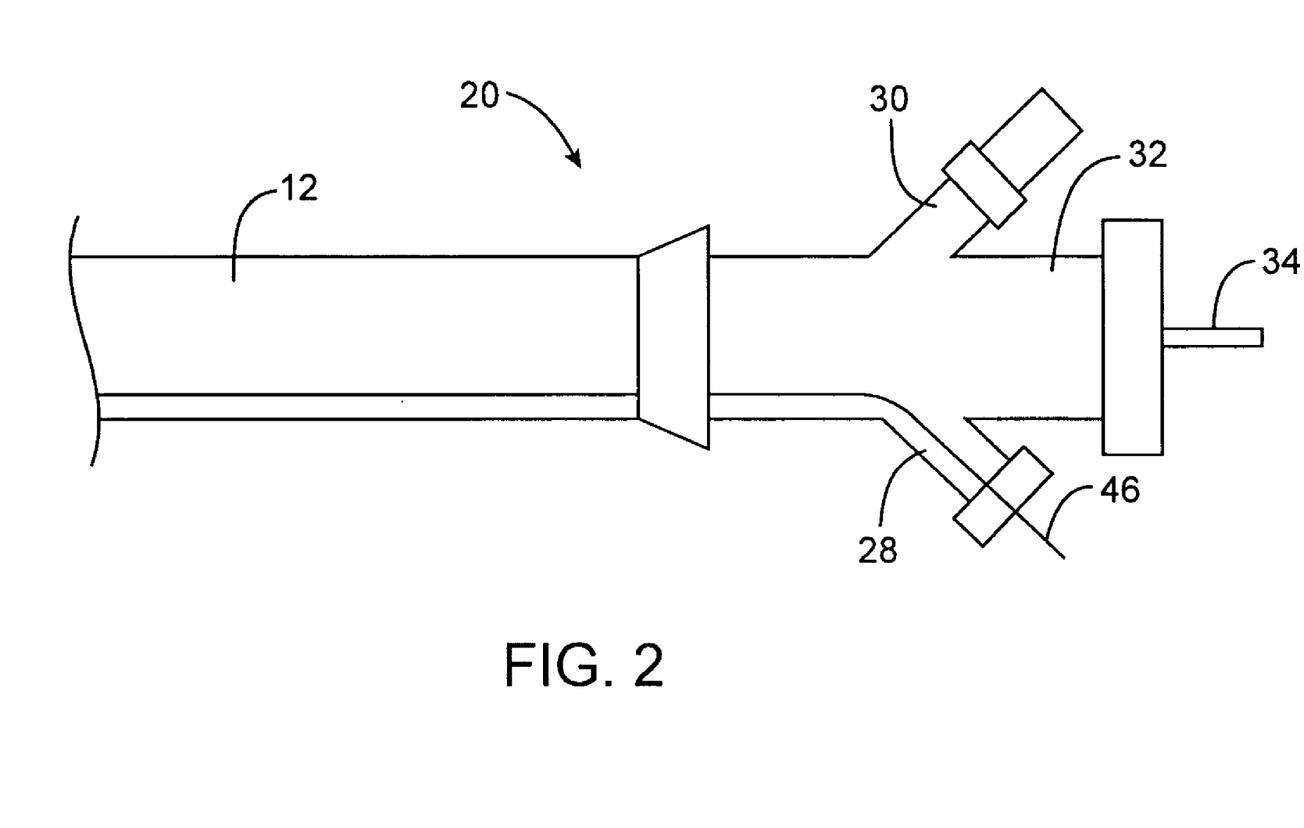
FIG. 2 shows a proximal port assembly of the present invention.

FIG. 1 shows one embodiment of a steerable distal support system 10 encompassed by the present invention. The steerable distal support system 10 generally includes an elongate body 12 having a proximal portion 14, a more flexible intermediate portion 16, and a steerable flexible distal tip 18. A proximal port assembly 20 may be removably or integrally coupled to the proximal portion 14 (FIG. 2).

Proximal portion 14 is comprised of a proximal tube, typically a hypotube. A distal end of the proximal portion 14 is coupled to proximal end of intermediate portion 16. A distal end of the intermediate portion 16 may be coupled to a proximal end of a distal flexible tip 18. Proximal portion 14 is typically the most stiff portion and may or may not comprise spiral coils. Intermediate portion 16 typically has spiral etchings that form coils 22 and at least a portion of the intermediate portion has a greater flexibility than proximal portion 14. A distal end of the proximal portion 14 and a proximal end of the intermediate portion 16 (e.g., an elongate coil body) may comprise coupling members 24 that allow for coupling between the proximal portion 14 and intermediate portion 16. In the illustrated embodiment, proximal portion 14 and intermediate portion are threadedly coupled to each other.

A distal end of the intermediate portion 16 may be coupled to a proximal end of the flexible distal tip 18. Similar to above, the distal end of the intermediate portion 16 and the proximal end of the flexible distal tip 18 may comprise a coupling members 26 that allow for coupling between the intermediate portion 16 and the flexible distal tip 18. In the illustrated embodiment, the intermediate portion 16 and the flexible distal tip 18 are threadedly connected to each other. It will be appreciated, however, that the proximal portion 14, intermediate portion 16, and distal tip 18 may be connected to each other by any other conventional means, such as solder, adhesive, or the like.

A proximal end of the proximal portion 14 of the steerable distal support system 10 can be coupled to a proximal port assembly 20. As shown in FIG. 2, the port assembly 20 can be a three-armed port assembly. The port assembly 20 may include a first arm 28 that houses a steering pull wire 46 that can control the steering/deflection of the distal tip 18. A second arm 30 can be used to receive an additional pull wire (not shown) or it may be used to aspirate (e.g., coupled to a vacuum source) or infuse the target site (e.g., coupled to a medical fluid source). The port assembly 20 may further comprises a third arm 32 can be used to receive a guide wire 34. The proximal port assembly 20 may be fixedly attached to the elongate body 12 or it may be removably attached to the elongate body 12.

In some embodiments the flexible distal tip 18 is approximately one half centimeter in length and steerable in one direction. In other embodiments, the distal tip 18 can longer or shorter in length, and may be steerable in one direction, two directions, three directions, four directions, or the like. A guidewire or a device for treating lesions can be disposed within an axial lumen 36 (FIG. 3) of the elongate body 12 so that it can be axially advanced to the occlusion so as to remove material from the body lumen (not shown). Some exemplary devices that may be received in the axial lumen include, but are not limited to, guidewire, infusion guidewire, clot maceration guidewire, normal guidewires of varying stiffness, devices for treating lesions, and the like. One exemplary guidewire that may be received within the axial lumen of the steerable distal support system 10 is described in co-pending and commonly owned U.S. Patent application Ser. No. 09/644,201, filed Aug. 22, 2000, the complete disclosure of which was previously incorporated herein by reference.

As shown in FIG. 1, a radio-opaque marker 38, such as platinum-iridium marker can be positioned on the flexible distal tip 18 to improve visibility under fluoroscopy. Preferably, the radio-opaque marker 38 is positioned on the distal most end of the distal tip 18.

As noted above, the steerable distal support system 10 typically defines an axial lumen 36. Axial lumen 36 may be used for infusion or aspiration. Since at least a portion of the intermediate portion 16 and flexible distal tip 18 are etched to create spiral coil windings 22, if the etchings go completely through the intermediate portion 16 and/or the flexible tip 18, it may be possible for the infusion fluid to leak out between the spiral coils 22 before it reaches the distal tip 18. Consequently, at least a portion of the elongate body 12 may comprise at least one of an inner tubing 40 and an outer tubing 42 to provide a flexible, structural support that prevents liquids from moving between the blood vessel and the axial lumen 36 of the elongate member 12. In the embodiment illustrated in FIG. 3, the steerable distal support system comprises both an inner tubing 40 and an outer tubing 42. In some embodiments, the outer tube 42 can be shaped to have one or more elbow openings 44 (FIG. 1) that facilitates bending of the distal tip 18 in the direction of the elbow opening 44. In other embodiments, the elongate body 12 may comprise only one of the inner tubing 40 and the outer tubing 42.

The inner tubing 40 typically comprises a polyimide or Teflon® tubing having a wall thickness of about 0.001 inches to about 0.0005 inches. An inner surface of the inner tubing 42 may be coated with Teflon® or other materials to improve movement of the guidewire or interventional devices through the axial lumen 36. Similarly, the outer surface of the outer tubing 42 may optionally be coated with Teflon® or other biocompatible materials to facilitate advancement of the steerable distal support system 10 through the body lumen.

Figure 3:
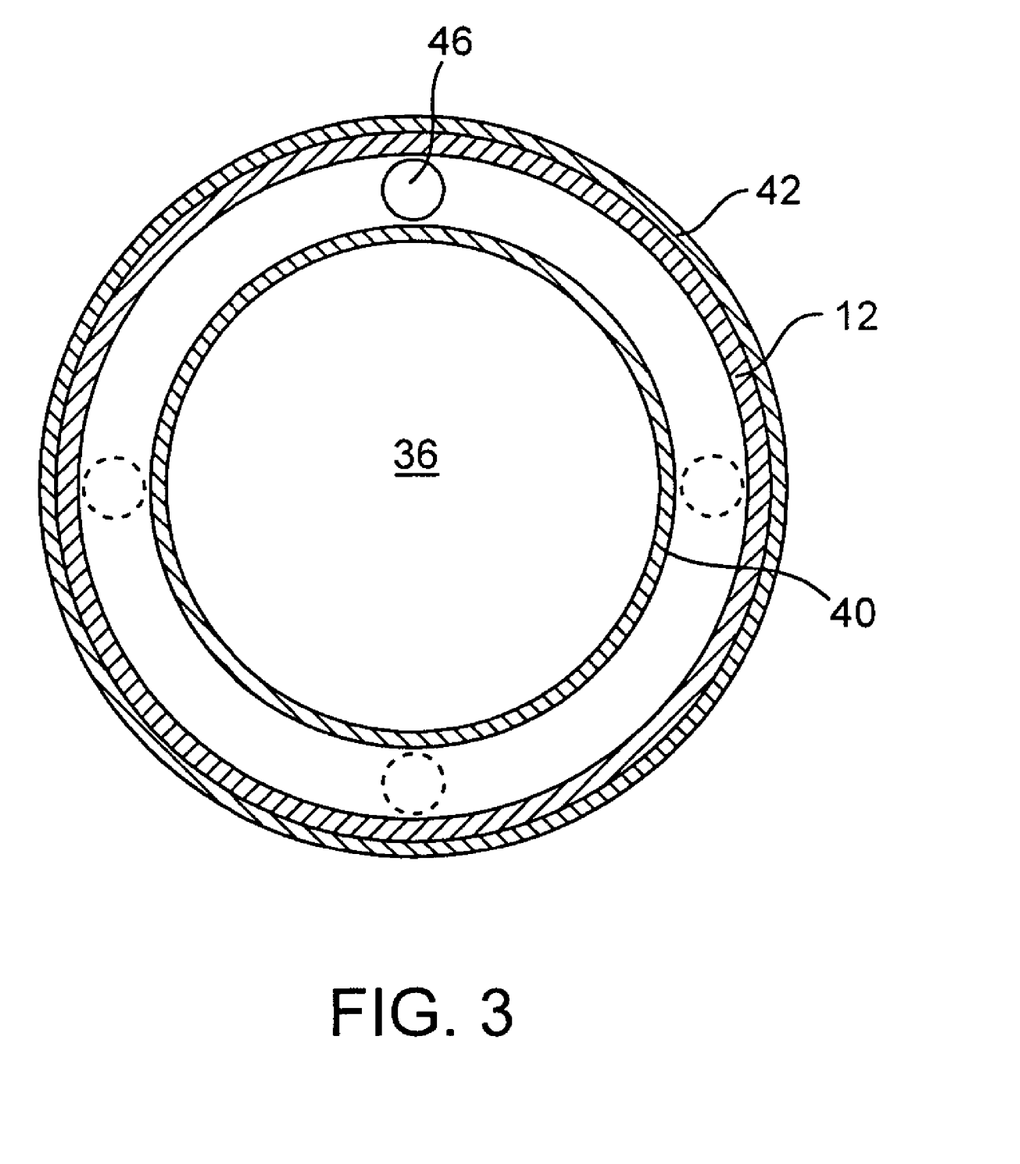
FIG. 3 is a cross sectional view of the distal tip along line 3-3.

Referring now to FIGS. 1-3, a pull wire(s) 46 extend through the proximal port assembly 20 and is coupled to the steerable flexible distal tip 18. Deflection of the distal tip 18 is controlled by the user actuated pull wire 46. The pull wire 46 typically extends from the proximal port assembly 20 through the elongate body 12 and connects to the distal end of the distal tip 18. The pull wire 46 can extend parallel to and offset from a longitudinal axis of the elongate body, such that axial actuation (e.g., pulling or rotating an actuator to cause proximal movement) of the pull wire 46 can deflect the distal tip 18 in the direction of the pull wire 46. As shown in phantom in FIG. 3, in some embodiments a plurality of pull wires 46 can be positioned around the longitudinal axis of the elongate body to provide a distal tip 18 that is deflectable in multiple directions. In such embodiments, the proximal port assembly may comprise an arm for each of the pull wires (not shown).

To shield the pull wire 46 from a guidewire and/or other interventional devices positioned within the axial lumen 36, the pull wire 46 may be positioned between the inner tubing 40 and the elongate body 12. In embodiments that do not include an inner tubing 40, the pull wire will be positioned within the axial lumen 36 that is defined by the inner surface of the proximal portion 14, intermediate portion 16 and flexible distal tip 18.

In an exemplary embodiment, the pull wire 46 has a diameter between 0.003 inches and 0.007 inches and is in the form of a strip or solid or braided wire. In one embodiment, the pull wire 46 is composed of 304SS Hyten®. The pull wire 46 preferably can withstand more than 400 kpsi of tensile force. It should be appreciated however, that the pull wire 46 can be modified to have a smaller or larger diameter and can be made from an alternative material, if desired. For example, the pull wire 46 can be comprised of a strip of stainless steel that can be moved longitudinally to deflect the distal tip 18. In one configuration, the pull wire 46 is soldered or otherwise connected to the distal end of flexible tip 18 and the remainder of the pull wire 46 extends proximally to the housing port assembly 20. To reduce the profile of the distal tip 18 and to increase the area of contact between the distal tip and the pull wire, the distal end (or the complete body) of the pull wire 46 can be flattened.

Manipulation of the proximal end of the pull wire 46 allows the user to deflect or steer the distal tip 18 without permanently impairing the inner structure of the steerable distal support system 10. The deflectable distal tip 18 provides a user with greater intraluminal control of navigating and steering the steerable distal support system to the target site. In other configurations, the pull wire is 46 can be soldered or otherwise connected to both the distal end of the distal tip 18 and to the junction between the intermediate portion 16 and distal tip 18. Therefore, if the distal tip 18 somehow breaks, the attached pull wire 46 can prevent the tip 18 from detaching from the steerable distal support system 10. A more complete description of the catheter can be found in commonly owned U.S. patent application Ser. No. 09/030,657, filed Feb. 25, 1998, the complete disclosure of which was previously incorporated by reference.

Figure 4:
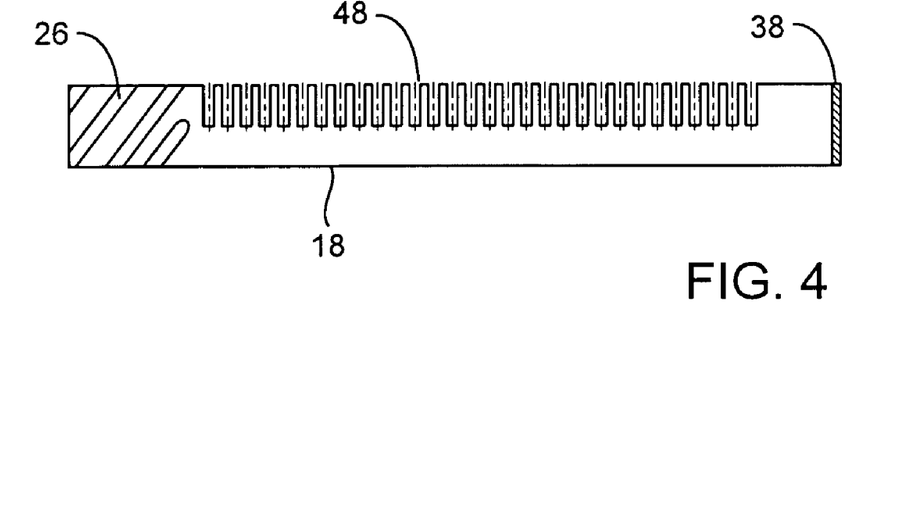
FIG. 4 shows a distal tip having ribs.
Figure 5:
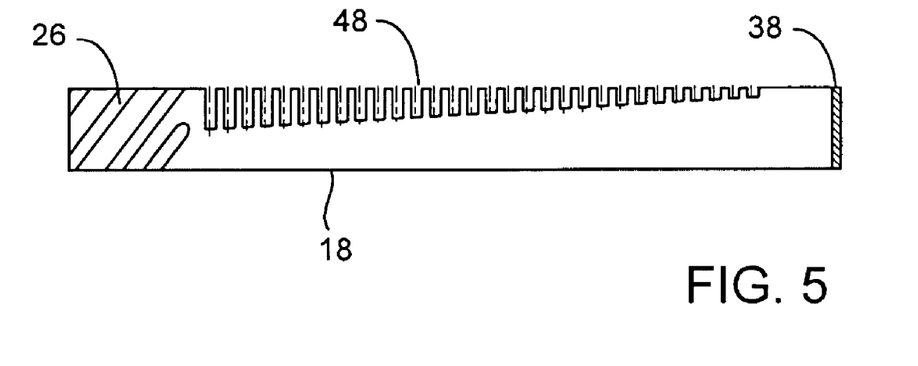
FIG. 5 shows an alternative distal tip having tapered ribs.

As shown in FIGS. 4 and 5 the distal tip 18 can be laser etched to have ribs or partial circumferential slots 48 formed on at least one side of the distal tip 18. As shown in FIG. 4 the ribs 48 can extend evenly along one side of the distal tip 18 to provide means for deflecting or flexing of the distal tip in the direction of the ribs. It should be appreciated, the size of the distal tip can be varied so as to accommodate larger and smaller body lumens. In the exemplary embodiment shown, there are thirty ribs 48 formed in the distal tip 18. It should be appreciated that any number of ribs can be created on the distal tip to facilitate steering. While not shown, in other embodiments, the ribs 48 can also be formed on opposite sides of the distal tip 18 so as to facilitate deflecting in two directions. Such ribs 48 can be spaced from the opposite ribs so as to not detrimentally effect the structural strength of the distal tip 18. Additionally, as mentioned above, some embodiments of the distal tip 18 can be steerable in four directions or more. Consequently, ribs 48 can be formed in a plurality of places on the distal tip 18 and additional pull wires 46 can be added to facilitate steering in multiple directions.

FIG. 5 shows an alternative embodiment of the distal tip 18 of the steerable distal support system 10. The ribs 48 can be tapered towards a distal end of the distal tip 18 to provide better control of the steering of the distal tip 18. The tapered ribs 48 provide a larger bend radius at the proximal end of the tip 18 while having a smaller bending radius at the distal end. Alternatively, the ribs 48 can be tapered toward a proximal end of the tip (not shown) to provide another variation to the steering of the distal tip. With such a variation, there will be a larger bending radius at the distal end of the tip and a smaller bending radius at the proximal end of the tip 18.

Figure 6:
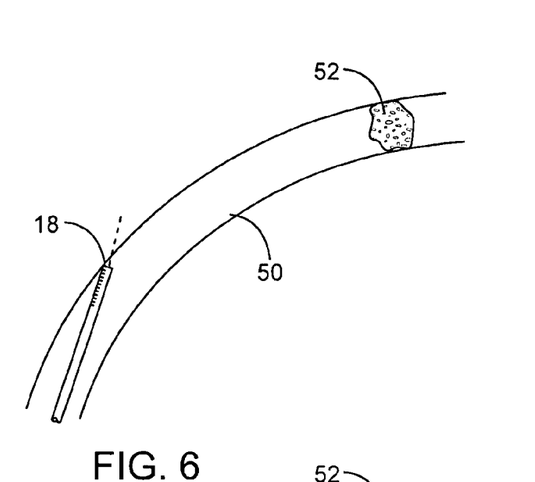
FIGS. 6-8 illustrate a method of advancing the guidewire system through a body lumen.
Figure 7:
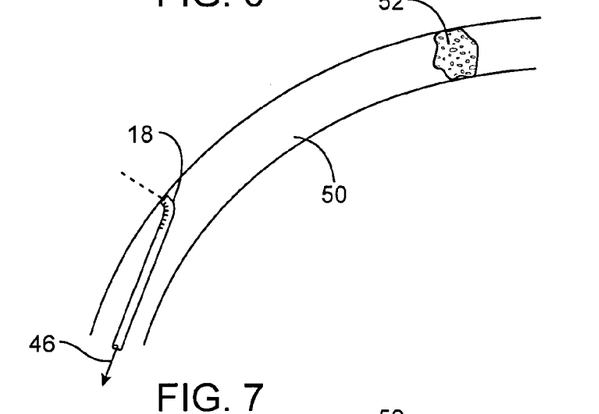
Figure 8:
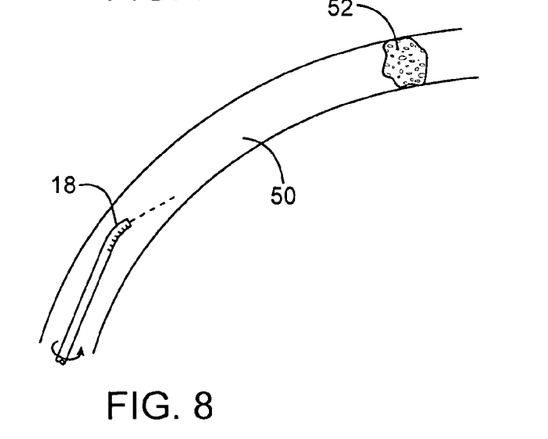

FIGS. 6 to 8 illustrate a method of use. The steerable distal support system can be introduced into the body lumen 50 using conventional delivery techniques. The distal tip 18 can be deflected and the elongate body may be torqued to navigate the steerable distal support system through the body lumen 50 to the occlusion 52. To deflect the distal tip 28, a user will cause axial movement of the pull wire until the distal tip 18 is deflected in the desired direction. In exemplary embodiments, the distal tip 18 is deflectable between approximately 5 degrees and 10 degrees. It should be appreciated however, that in other embodiments it may be possible to steer the distal tip up to 180 degrees. For example, as illustrated in FIG. 6, as the catheter is being advanced through the body lumen, the distal tip 18 may contact a curved portion of the body lumen wall. As shown in FIG. 7, to get past the curved, tortuous portion of the body lumen, the user can then activate the pull wire to deflect the distal tip to change the direction of advancement (as shown by the dotted line). To continue advancement, the user can twist or torque the proximal end of the catheter system until the distal tip is torqued and clear of the body lumen wall and aligned with the body lumen (FIG. 8). Thereafter, the user can push the proximal end of the catheter system and continue advancement through the body lumen 50 to the occlusion 52. When the occlusion has been reached, a device within the axial lumen 36 of the steerable distal support system can be advanced out of the axial lumen 36 to treat the occlusion.

Figure 9:
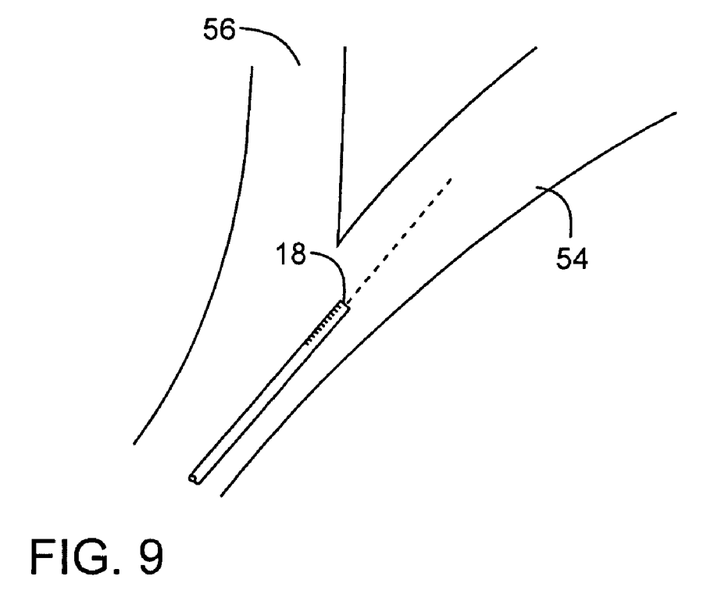
FIGS. 9-10 illustrate advancing through a bifurcated body lumen.
Figure 10:
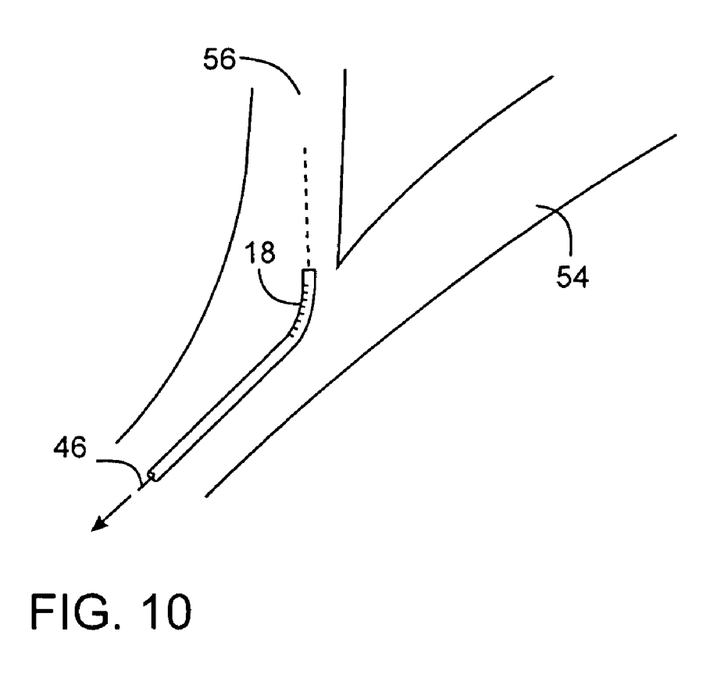

In another method, the deflectable distal tip allows deflection of the distal tip to steer the catheter system through the correct branch vessel of the body lumen. As shown in FIG. 9, if the steerable distal support system 10 is advanced in its current orientation, the steerable distal support system will be advanced down the right branch vessel 54. In order to be moved up through the left branch vessel 56, the tip 18 can be deflected and the steerable distal support system may be torqued (if needed) to move the steerable distal support system 10 into alignment with the left branch vessel 56. Accordingly, in the orientation of the steerable distal support system 10 shown in FIG. 10, advancement of the steerable distal support system 10 will move the steerable distal support system 10 into the left branch vessel 56.

Figure 12:
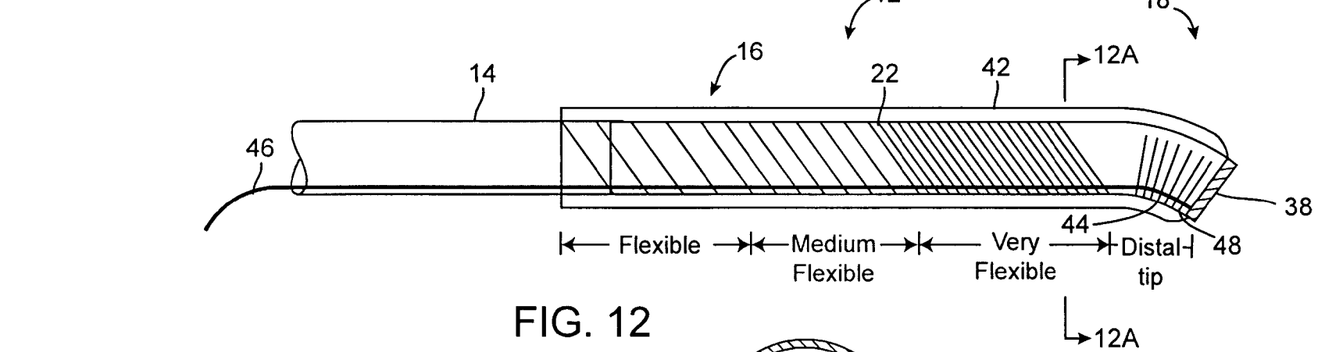
FIG. 12 illustrates deflection of the distal tip of the embodiment of FIG. 11.
Figure 12A:
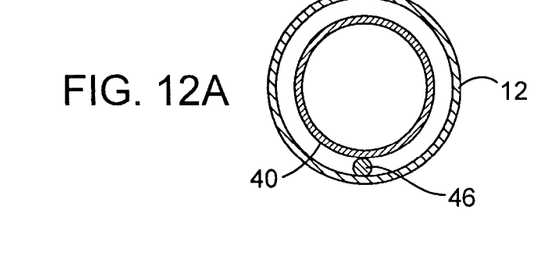
FIG. 12A is a cross sectional view of the distal portion of the embodiment of FIG. 12 along lines 12A-12A.

FIGS. 11 to 12A illustrate another embodiment of a steerable distal support system encompassed by the present invention. In the embodiment illustrated in FIGS. 11 and 12, the elongate body 12 (e.g., proximal portion 14, intermediate portion 16, and flexible distal tip 12) are integrally formed from a single, laser etched hypotube. As illustrated, the proximal portion 14 is the stiffest and does not substantially have laser etchings or coils, and is substantially in the form of a tube. The intermediate portion 16 has a varying laser etching to create coils 22 in which the pitch decreases distally along the length of the intermediate portion, so that the intermediate portion provides varying degrees of (e.g., increasing) flexibility along the length of the intermediate portion. In the illustrated embodiment, the intermediate portion 16 comprises a three different regions of flexibility—flexible, medium flexible, very flexible. As can be appreciated, other embodiments of the intermediate portion may have only one or two regions of flexibility or may have more than three regions of different flexibility, depending on the desired characteristics of the steerable distal support system 10.

The unibody design of the embodiment in FIGS. 11 and 12 provides for a smooth transition between the stiffer proximal portion and the more flexible intermediate portion and the distal tip and eliminates the joints and potential points of weakness that are present between interconnected proximal portion 14, intermediate portion 16 and distal tip 18 of the embodiments of FIGS. 1 to 10. Additionally, the unibody design provides for improved torque transmission between the proximal end of and the distal tip and reduces the potential for fracture during torquing of the steerable distal support system 10.

Similar to the previous embodiment, elongate body 12 may comprise an inner tubing 40 (FIG. 12A) and/or an outer tubing 42 to maintain the flow of an infusion fluid within the axial lumen 36 of the steerable distal support system. In the illustrated embodiment, the outer tubing 42 extends over the spiral etchings and coils 22 in the intermediate portion 14 and extend over at least a portion of the distal tip 18. The outer tubing 42 may comprise a window 44 over the slots or ribs 48 on the distal tip 18 to allow for deflection of the steerable distal tip 18 without causing stretching or bunching of the outer tubing 42 during the deflection.

Similar to the embodiment o FIG. 1, proximal movement of the pull wire 46 causes a deflection of the distal tip 18. Torquing of the proximal port assembly will cause torquing (typically 1:1) of the distal tip 18. The position of the distal tip 18 may be monitored by fluoroscopic monitoring of a radiopaque marker 38 that is positioned at the distal end of the distal tip 18.

Figure 14:
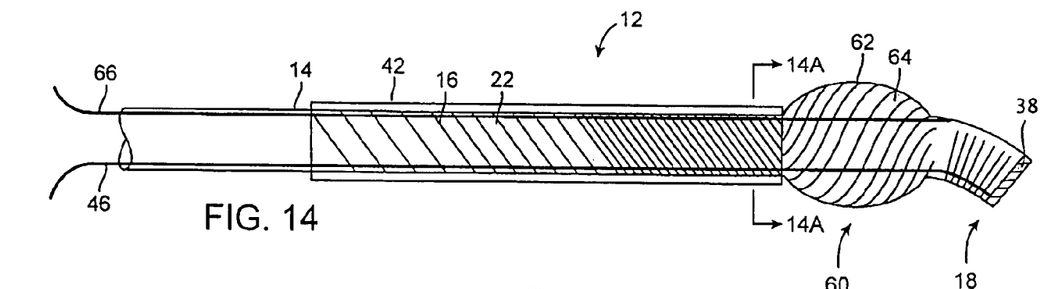
FIG. 14 illustrates deflection of the distal tip and expansion of the expandable basket of the steerable distal support system of FIG. 13.

Another embodiment of a steerable distal support system that is encompassed by the present invention is illustrated in FIGS. 13-14. The embodiment illustrated in FIGS. 13-14 include a centering assembly. The centering assembly is in the form of an expandable centering basket 60 that comprises slots 62 between a plurality of expandable struts 64. The centering basket 60 allows the physician to anchor, stabilize and substantially center the elongate body 12 of the steerable distal support system within the body lumen while the heart is beating. Additionally, the centering basket 60 allows positioning of the steerable distal support system 10 in the center of the occluded vessel while blood is allowed to flow through the body lumen in spaces 62 around spaced apart struts 64 of the centering basket.

While the embodiments of FIGS. 13-15 will be described in terms of a single, laser etched hypotube, it should be appreciated that the steerable distal support system 10 of FIGS. 13-14 may also be comprised of a plurality of interconnected tubes (similar to FIG. 1).

Similar to the embodiments in FIGS. 1 and 11, the embodiment of FIG. 13 comprises a proximal portion 14, an intermediate portion 16 and a steerable distal tip 18. Similar to the other embodiments, the flexible intermediate portion 16 comprises spiral etchings that create coils 22 in the flexible intermediate portion 16. The distal flexible tip 18 may comprise one or more sets of slots 48 to facilitate bending.

Additionally, a centering assembly, in the form of a centering basket 60 is positioned between the steerable distal tip 18 and the flexible intermediate portion 16. In preferred embodiments, the centering basket 60 is integrally formed from the same tubing that forms the distal tip 18 and intermediate portion 16. The centering basket 60 is formed in the hypotube by forming substantially curved or S-shaped openings or slots 62 so as to create a plurality of S-shaped struts 64. The struts maybe substantially evenly spaced. Typically, the slots 62 between the struts 64, in an unexpanded configuration, will have a width between about 0.0002 inches and about 0.0005 inches. As can be appreciated, it may be possible to form other sized or shaped slots 62 to form the struts 64 of the centering basket 60 (e.g., linear slots), but Applicants have found that the S-shaped slots 62 create struts 64 that do not kink or collapse when expanded.

If an outer tubing 42 is present, the outer tubing 42 may be disposed over the intermediate portion 16, but will not typically extend over the centering basket 60. In contrast, if an inner tubing 40 is present, the inner tubing 40 will typically extend through the intermediate portion and through the centering basket 60. However, in other embodiments, it may be possible to have the inner tubing 40 extend to a portion that is proximal of the centering basket 60.

Unlike conventional balloons, the centering basket 60 is composed of a plurality struts 64 that are separated by S-shaped slots 62. Consequently, when the centering basket 60 is in an expanded configuration (typically having the struts contacting the inner surface of the body lumen), blood will be allowed to flow through the S-shaped slots 62. Advantageously, unlike conventional balloons, the centering basket will not substantially interfere with the normal blood flow through the body lumen. The centering basket 60 is of particular importance when the centering basket 60 is positioned within a body lumen directly over peripheral blood vessels. Because of the slots 62 between the struts, blood will be allowed to flow through the primary blood vessel and the peripheral blood vessels.

Figure 15A:
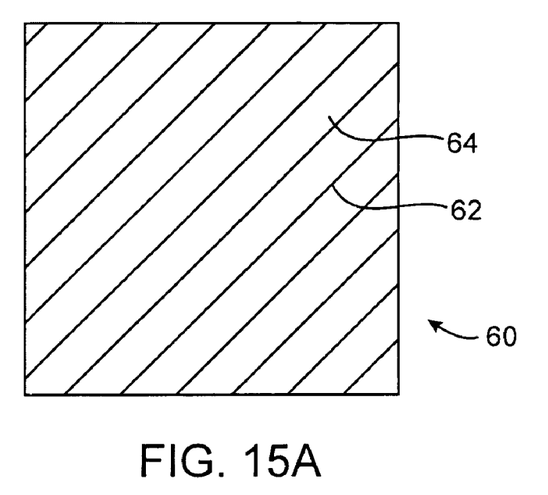
FIGS. 15A, 15B, 15C illustrate the expandable basket encompassed by the present invention.
Figure 15B:
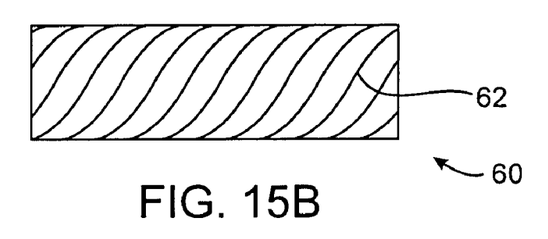
Figure 15C:
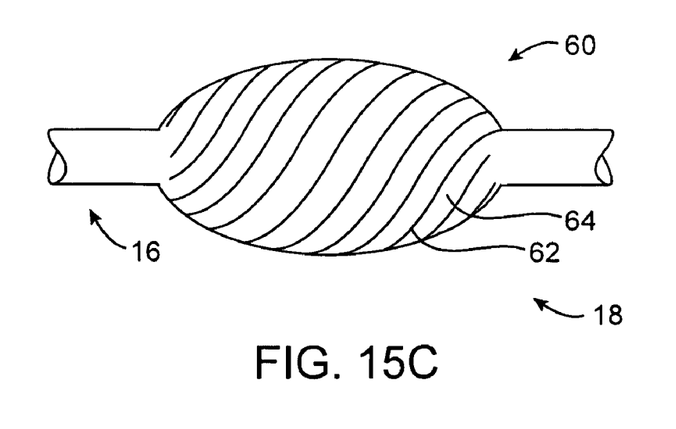

FIGS. 15A is a flattened view of the hypotube which illustrates that the slots 62 are diagonal slots (relative to the longitudinal axis of the elongate body). FIG. 15B illustrates a side view of an unexpanded centering basket 60 in which the diagonal slots are substantially curved (e.g., S-shaped) when in a tubular shape. FIG. 15C illustrates an expanded centering basket 60.

Figure 14A:
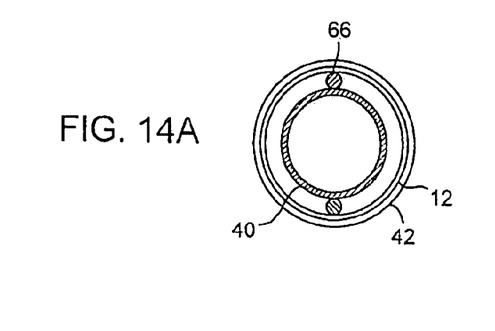
FIG. 14A is a cross sectional view of the distal portion of the embodiment of FIG. 14 along the lines 14A-14A.
Figure 16:
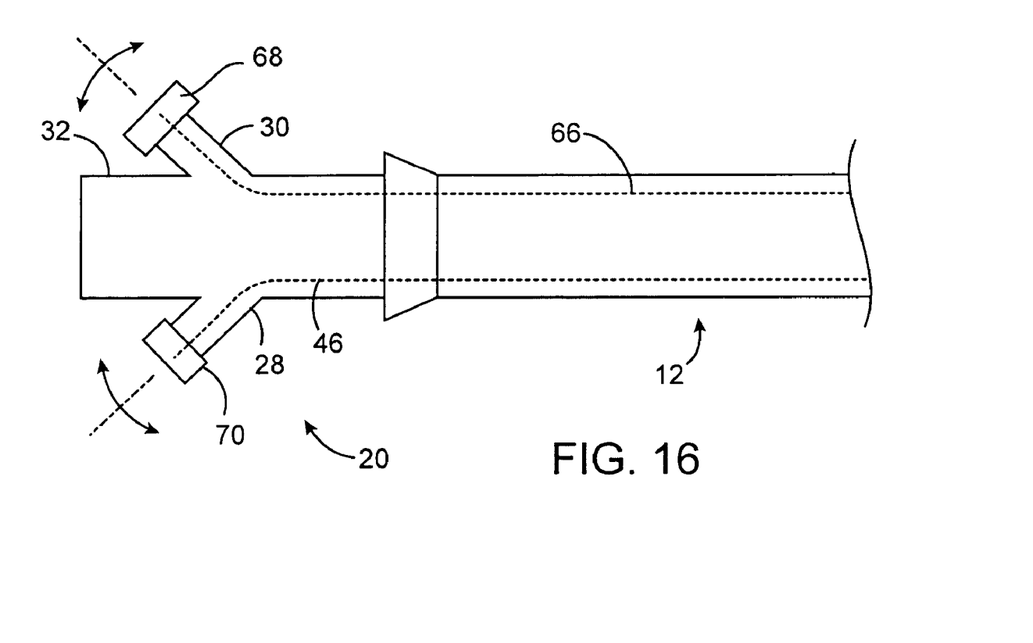
FIG. 16 illustrates a port assembly for use with the embodiment of FIG. 13.
Figure 16A:
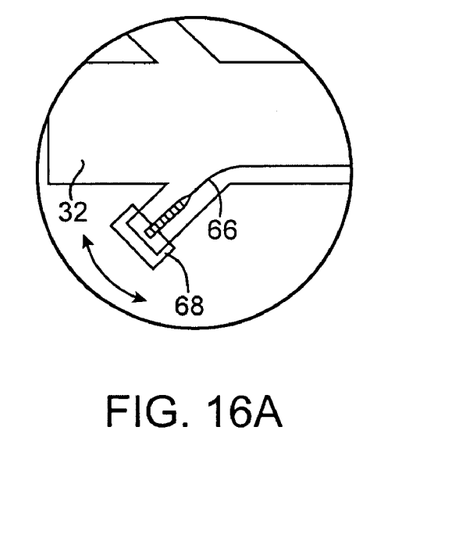
FIG. 16A illustrates a method of actuating the second pull wire.

FIGS. 16 and 16A illustrate one proximal port assembly 20 that may be used to actuate deflection of the distal tip 18 and expansion of the centering basket 60. To expand the centering basket 60 from an unexpanded configuration (FIG. 13) to an expanded configuration (FIG. 14), a second pull wire 66 may be coupled to a distal end of the centering basket 60. As shown in FIG. 14A, the second pull wire 66 may be disposed between the elongate body 12 and the inner tubing 40. If no inner tubing 40 is present, the second pull wire 66 may be merely be positioned within the axial lumen 36 of the elongate body 12. A proximal end of the second pull wire 66 may be coupled to the expandable basket knob 68 that is positioned on the second arm 30 of the proximal port assembly 20 (FIG. 16). To activate the expansion of centering basket 60, the centering basket knob 68 that is attached to second arm 30 is actuated so that the second pull wire 66 is moved proximally. Proximal movement of the second pull wire 66 pulls the distal end of the struts 64 closer to the proximal end of the struts 64 so as to cause the center of the struts 64 to move radially and expand the centering basket 60.

In one specific configuration, knob 68 may include a screw-like mechanism for coupling to the second pull wire 66. Rotation of the expandable basket knob 68 and screw like mechanism causes proximal movement of the second pull wire 66 and expansion of the centering basket. Counter rotation of knob 68 causes the centering basket to move back to its unexpanded configuration (FIG. 13). Similarly, rotation of the deflectable tip knob 70 causes deflection of the distal tip 18, and counter rotation of the deflectable tip knob 70 causes the distal tip 18 to move back toward its straight configuration. As can be appreciated, a variety of other knobs or input devices may be used to actuate the centering basket and the distal tip, and the port assembly 20 of the present invention is not limited to rotatable knobs.

Figure 17:
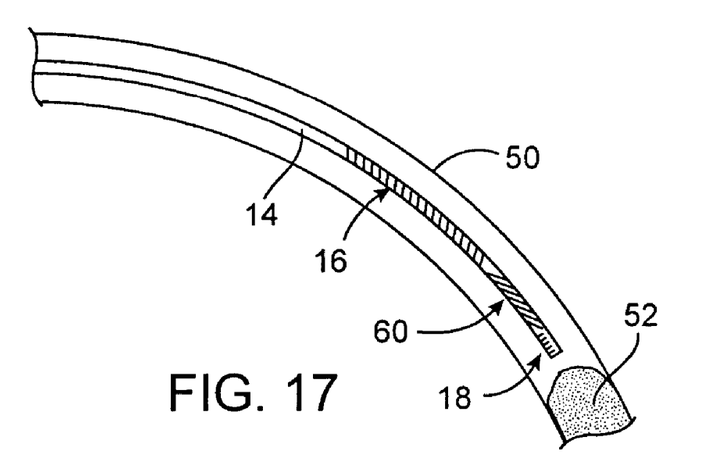
FIGS. 17 and 18 illustrate a method of use of the embodiment of FIG. 14.
Figure 18:
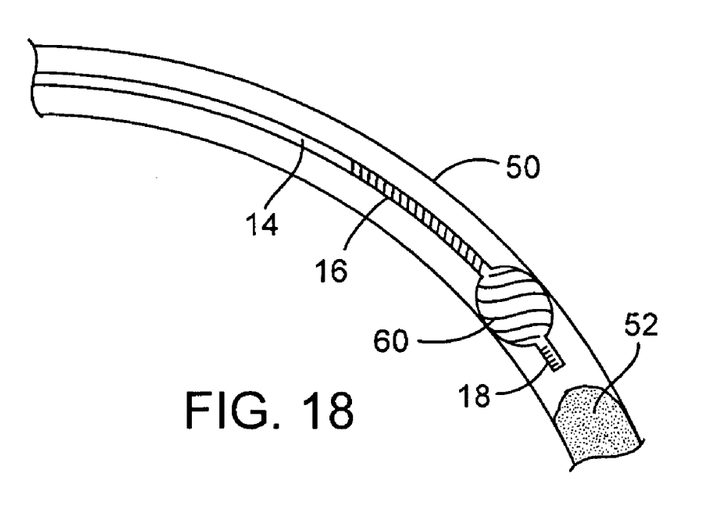

FIGS. 17 and 18 illustrate a simplified method of the present invention. In FIG. 18, the steerable distal support system is advanced through the body lumen 50 to the occlusion 52 using the deflectable distal tip to steer the steerable distal support system 10 through the body lumen (described above). During advancement through the body lumen, the centering basket 60 will generally be in an unexpanded configuration. Once the occlusion 52 is reached, the expandable basket knob 68 is rotated so as to move the second pull wire 66 proximally and expand the centering basket 60 (FIG. 18). The centering basket 60 may be expanded so that the struts 64 contact the inner wall of the body lumen so as to stabilize and anchor the distal end of the steerable distal support system 10. If needed, the distal tip 18 can thereafter be deflected so that the distal end is properly positioned relative to the occlusion 52. Thereafter, an interventional device may be advanced through the axial lumen of the steerable distal support system 10 to treat the occlusion 52.

Figure 19:
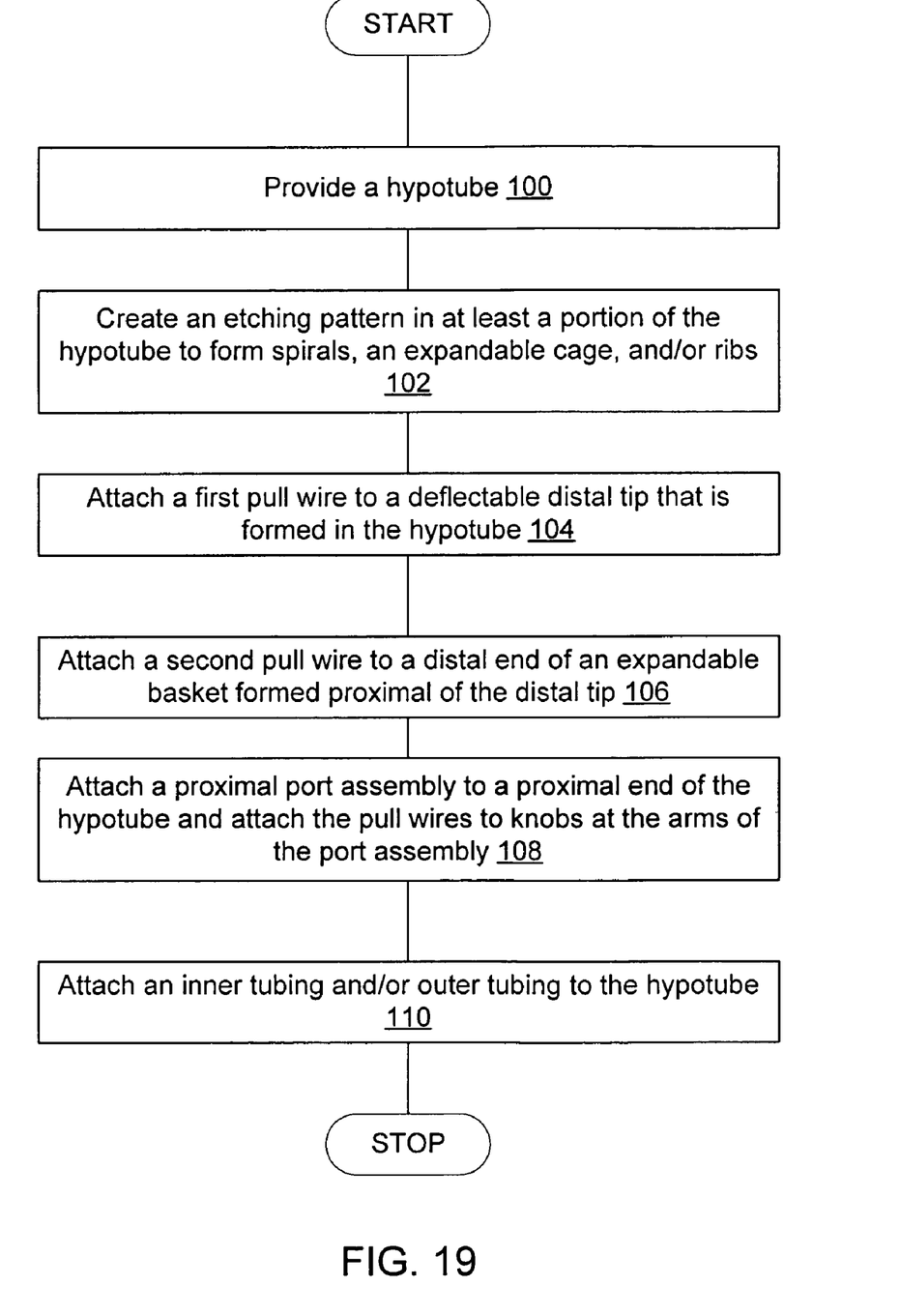
FIG. 19 schematically illustrates an example of a simplified method of manufacturing a steerable distal support system.

FIG. 19 illustrates a simplified flow chart of one exemplary method of manufacturing the steerable distal support system of the present invention. At 100, a hypotube is provided. At 102, the hypotube is laser etched on at least a portion to form the intermediate spirals, and the ribs on the distal tip. Optionally, the hypotube may be laser etched to form the expandable basket. At 104, the first pull wire is attached to the deflectable distal tip. At 106, a second pull wire is optionally attached to a distal end of the expandable basket. The first and second pull wires are directed down an axial lumen of the hypotube and are attached to a proximal port assembly that is coupled to a proximal end of the hypotube 108. The pull wires are attached to knobs that are positioned on arms of the port assembly. As noted above, a screw-like assembly may be coupled to the knobs so that rotation of the knobs cause proximal pulling on the pull wires. At 110, an inner tubing and/or an outer tubing may be coupled to the elongate body.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A steerable distal support system comprising:
   an elongate body comprising a proximal portion, an intermediate portion, and a deflectable distal tip integrally formed by slots on the body;
   an expandable centering element integrally formed by slots in the elongate body proximal of the deflectable distal tip, and which is configured for centering the portion of the elongate body when the centering element is in an expanded configuration;
   a first pull wire fixedly attached to the distal tip of the elongate body, wherein pulling of the first pull wire deflects the distal tip; and
   a second pull wire attached to the expandable centering element, wherein pulling of the second pull wire expands the expandable centering element.

2. The steerable distal support system of claim 1, wherein the slots of the expandable centering element define a plurality of expandable struts, wherein in an expanded configuration a portion of the struts expand radially outward from the elongate body and contact an inner surface of a body lumen and to open said slots between the struts.

3. The steerable distal support system of claim 2 wherein the slots between the struts are substantially S-shaped.

4. The steerable distal support system of claim 1 wherein the elongate body comprises a laser etched hypotube.

5. The steerable distal support system of claim 1, wherein slots of the expandable centering element comprise a spiral coil.

6. The steerable distal support system of claim 5, wherein the spiral coil comprises a decreasing pitch distally along an intermediate portion of the expandable centering element, wherein the decreasing pitch creates an increased flexibility in the intermediate portion of the expandable centering element.

7. The steerable distal support system of claim 1 further comprising a radiopaque marker positioned at a distal end of the deflectable distal tip.

8. The steerable distal support system of claim 1 wherein the proximal portion, intermediate portion, expandable centering element, and deflectable distal tip are comprised of a single hypotube.

9. The steerable distal support system of claim 1, further comprising
   at least either or both an inner liner and an outer liner coupled to at least a portion of at least one of an inner surface and an outer surface of the intermediate portion.

10. The steerable distal support system of claim 9, wherein the inner liner is connected to at least a portion of the intermediate member.

11. The steerable distal support system of claim 1, wherein the expandable centering element is configured for further stabilizing the elongate tubular member within a body lumen.

12. The steerable distal support system of claim 1, wherein the expandable centering element and the deflectable distal tip are formed from separate interconnected sections.

* * * * *